United States Patent
Kim et al.

[11] Patent Number: 5,990,335
[45] Date of Patent: Nov. 23, 1999

[54] DI-P-TOLYDIALKYLSILANE DERIVATIVE AND PHOTOLUMINESCENE POLYMER FORMED THEREFROM AND METHODS FOR PREPARING THESE COMPOUNDS

[75] Inventors: Hwan-kyu Kim; Soo-min Lee; Mi-kyung Ryu; Ki-dong Kim, all of Taejun, Rep. of Korea

[73] Assignee: Samsung Display Devices Co., Ltd., Kyungki-do, Rep. of Korea

[21] Appl. No.: 09/004,300

[22] Filed: Jan. 8, 1998

[30] Foreign Application Priority Data

Oct. 1, 1997 [KR] Rep. of Korea ............ 97-464

[51] Int. Cl.$^6$ ................ C07F 7/08; C07F 7/10
[52] U.S. Cl. ............ 556/415; 556/488; 556/489; 528/32
[58] Field of Search ............ 506/488, 489, 506/415; 528/488, 489, 415; 556/32

[56] References Cited

U.S. PATENT DOCUMENTS

| | | | |
|---|---|---|---|
| 3,334,122 | 8/1967 | Cekada et al. | 556/489 |
| 3,347,897 | 10/1967 | Webster | 556/489 |
| 3,558,683 | 1/1971 | Belsky et al. | 556/489 |
| 4,502,973 | 3/1985 | Stangroom | 252/73 |
| 5,621,130 | 4/1997 | Ando et al. | 556/465 |
| 5,741,921 | 4/1998 | Kreuder et al. | 556/406 |

*Primary Examiner*—Paul F. Shaver
*Attorney, Agent, or Firm*—Leydig, Voit & Mayer, Ltd.

[57] ABSTRACT

A di-p-tolyldialkylsilane derivative, a photoluminescence polymer formed from the derivative, and methods for preparing the derivative and polymer are provided. The di-p-tolyldialkylsilane derivative is represented by the following formula (1):

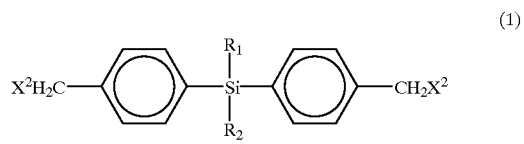

(1)

where $R_1$ and $R_2$ are independently selected from the group consisting of phenyl and $—(CH=CH)_k R_3$ (k is an integer between and inclusive of 0 and 2, and $R_3$ is hydrogen or alkyl), and $X^2$ is selected from the group consisting of hydrogen, halogen atom and cyano group. The di-p-tolylalkylsilane derivative of the formula (1) is very useful as a monomer of a functional polymer. The photoluminescence polymer formed from the di-p-tolylalkylsilane derivative of the chemical formula (1) contains a repeating unit having a silicon between the conjugated double bonds, thereby suppressing electron movement of the conjugated double bond. As a result, a range of colors between blue and green, particularly, blue, can be obtained. Also, when the photoluminescence polymer is adopted as a color-developing substance, the threshold voltage characteristics are improved.

13 Claims, 6 Drawing Sheets

DI-P-TOLYDIALKYLSILANE DERIVATIVE AND PHOTOLUMINESCENE POLYMER FORMED THEREFROM AND METHODS FOR PREPARING THESE COMPOUNDS

BACKGROUND OF THE INVENTION

1. Field of the Invention

The present invention relates to a di-p-tolyldialkylsilane derivative which is an organic silicon compound useful as a monomer of a functional polymer, a photoluminescence polymer formed therefrom, and methods for forming the di-p-tolyldialkylsilane derivative and the photoluminescence polymer.

2. Description of the Related Art

Recent advances in the information and communications industries have increased the need for high performance display devices. Generally, display devices are classified into luminous types and non-luminous types. Luminous type display devices include cathode ray tubes (CRT), electroluminescence displays (ELD) and light emitting diodes (LED); non-luminous type display devices include liquid crystal displays (LCD).

As an index of the basic performance of the display device, there are operating voltage, power consumption, luminance, contrast, response time, life span and display color, among others.

The LCD, as one of the non-luminous type display devices, has been most favored recently, due to its light weight and low power consumption. However, characteristics such as response time, contrast and viewing angle properties are unsatisfactory, leaving room for improvement. Meanwhile, the ELD has been focused as a next generation display device which can solve such problems.

The ELD, as one of the luminous type display devices, can be manufactured easily and requires a low driving voltage. In addition, the ELD can be made thin and mass-produced.

A color-developing substance used in the ELD includes an inorganic material and an organic material.

The inorganic material consumes more power, and emits yellow range color, so that an additional complicated process is required to display a full range of colors.

On the other hand, it is anticipated that the organic material can overcome the limitations of the inorganic material. As the organic material, poly(p-phenylenevinylene) (PPV) is known. However, such a compound includes a non-conjugated spacer group such as alkyl and ethylene oxide between photoluminescence groups, so that the threshold voltage is relatively high. When the threshold voltage is high, the photoluminescence polymer can be damaged, and it is difficult to drive the ELD adopting the photoluminescence polymer.

SUMMARY OF THE INVENTION

To solve the above problems, it is an object of the present invention to provide an organic silicon compound and a method for preparing the same.

It is another object of the present invention to provide a photoluminescence polymer having improved threshold voltage characteristics, and providing a wide range of colors between blue and green, and a method for preparing the same.

According to one aspect of the present invention, there is provided a di-p-tolyldialkylsilane derivative represented by the formula (1):

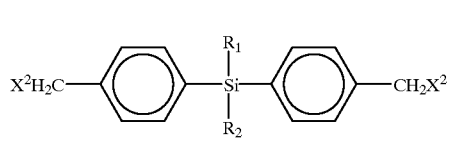

(1)

where $R_1$ and $R_2$ are independently selected from the group consisting of phenyl and $-(CH=CH)_k R_3$ (k is an integer from 0 to 2, and $R_3$ is hydrogen or alkyl), and $X^2$ is selected from the group consisting of hydrogen, a halogen atom and a cyano group.

According to another aspect of the present invention, there is provided a photoluminescence polymer comprising a repeating unit containing silicon between conjugated double bonds, represented by the following formula (2):

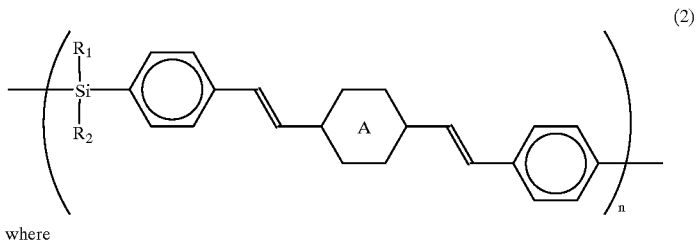

(2)

where

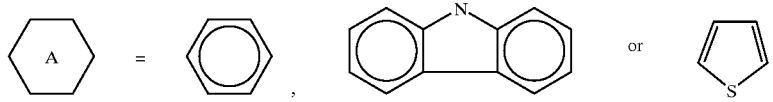

$R_1$ and $R_2$ are independently selected from the group consisting of phenyl and $-(CH=CH)_k R_3$ (k is an integer from 0 to 2, and $R_3$ is hydrogen or alkyl), $R_4$ is selected from the group consisting of hydrogen, an unsubstituted or substituted aliphatic hydrocarbon group, or an unsubstituted or substituted aromatic hydrocarbon group, and n is an integer from 1 to 100.

Preferably, the photoluminescence polymer is a compound represented by the formula (3) wherein

is benzene, and $R_1$ and $R_2$ are a phenyl group, a compound represented by the formula (4) wherein

is N-alkylcarbazole, and $R_1$ and $R_2$ are a phenyl group, and a compound represented by the formula (5) wherein

is thiophene, and $R_1$ and $R_2$ are a phenyl group.

where $R_4$ is selected from the group consisting of hydrogen, an unsubstituted or substituted aliphatic hydrocarbon group, or an unsubstituted or substituted aromatic hydrocarbon group, and n is an integer from 1 to 100.

According to still another aspect of the present invention, there is provided a method for preparing a di-p-tolyldialkylsilane derivative of the formula (1), the method comprising the steps of:

(a) reacting a dialkyldichlorosilane (A) with an organometallic compound (B) to obtain a di-p-tolyldialkylsilane (C); and (b) reacting the di-p-tolyldialkylsilane (C) with a halogenating agent or a cyanation agent,

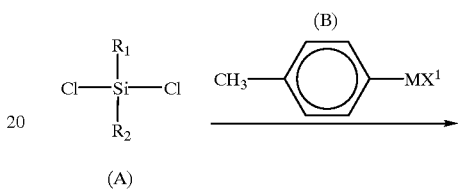

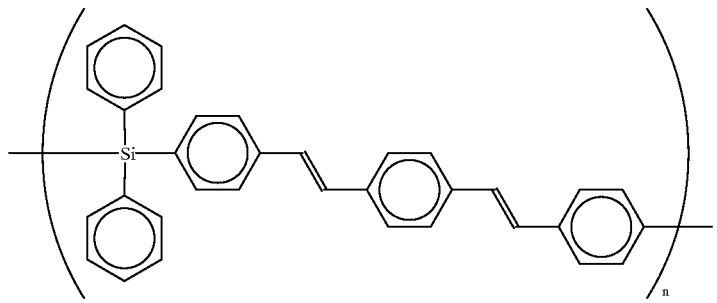

(3)

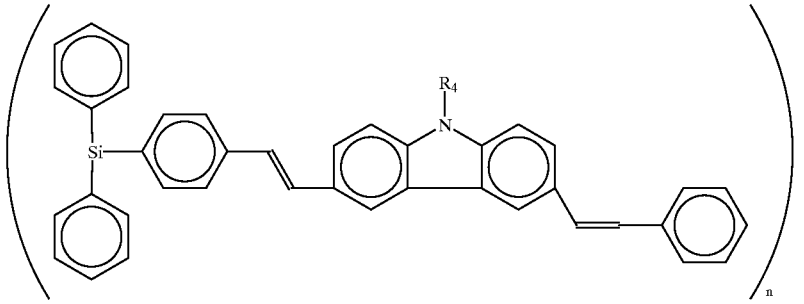

(4)

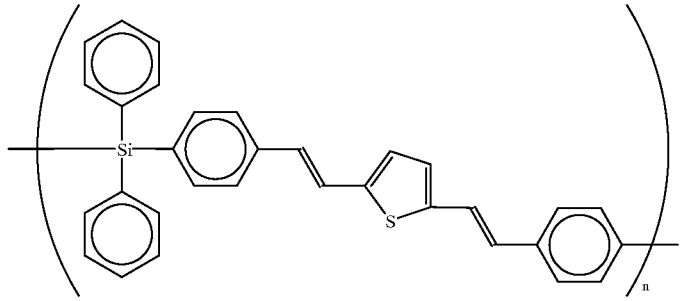

(5)

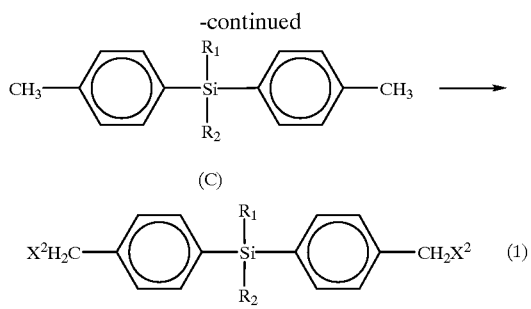

where $R_1$ and $R_2$ are independently selected from the group consisting of phenyl and $-(CH=CH)_kR_3$ (k is an integer from 0 to 2, and $R_3$ is hydrogen or alkyl group), M is magnesium (Mg) or lithium (Li), $X^1$ is chloride (Cl), bromide (Br) or iodide (I) and $X^2$ is hydrogen, Cl, Br, I or cyanide (CN).

According to yet still another aspect of the present invention, there is provided a method for preparing a photoluminescence polymer of the formula (2), the method comprising the steps of:

(a) reacting a di-p-tolyldialkylsilane derivative of the formula (1) with triphenylphosphine to form the corresponding phosphonium salt (D); and (b) reacting the obtained phosphonium salt (D) with a dialdehyde compound (E),

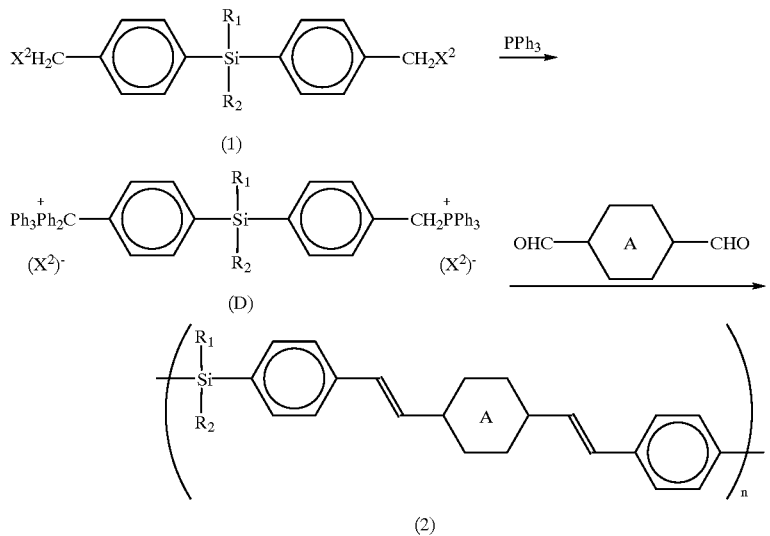

where

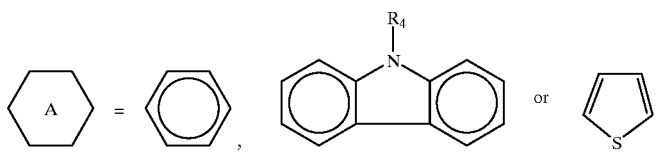

$R_1$ and $R_2$ are independently selected from the group consisting of phenyl and $-(CH=CH)_kR_3$ (k is an integer from 0 to 2, and $R_1$ is hydrogen or alkyl), $X^2$ is selected from the group consisting of hydrogen, a halogen atom and a cyano group, and $R_4$ is selected from the group consisting of hydrogen, an unsubstituted or substituted aliphatic hydrocarbon group, an unsubstituted or substituted aromatic hydrocarbon group, and n is an integer from 1 to 100.

BRIEF DESCRIPTION OF THE DRAWINGS

The above objects and advantages of the present invention will become more apparent by describing in detail preferred embodiments thereof with reference to the attached drawings in which.

DESCRIPTION OF THE PREFERRED EMBODIMENTS

Figure 1:
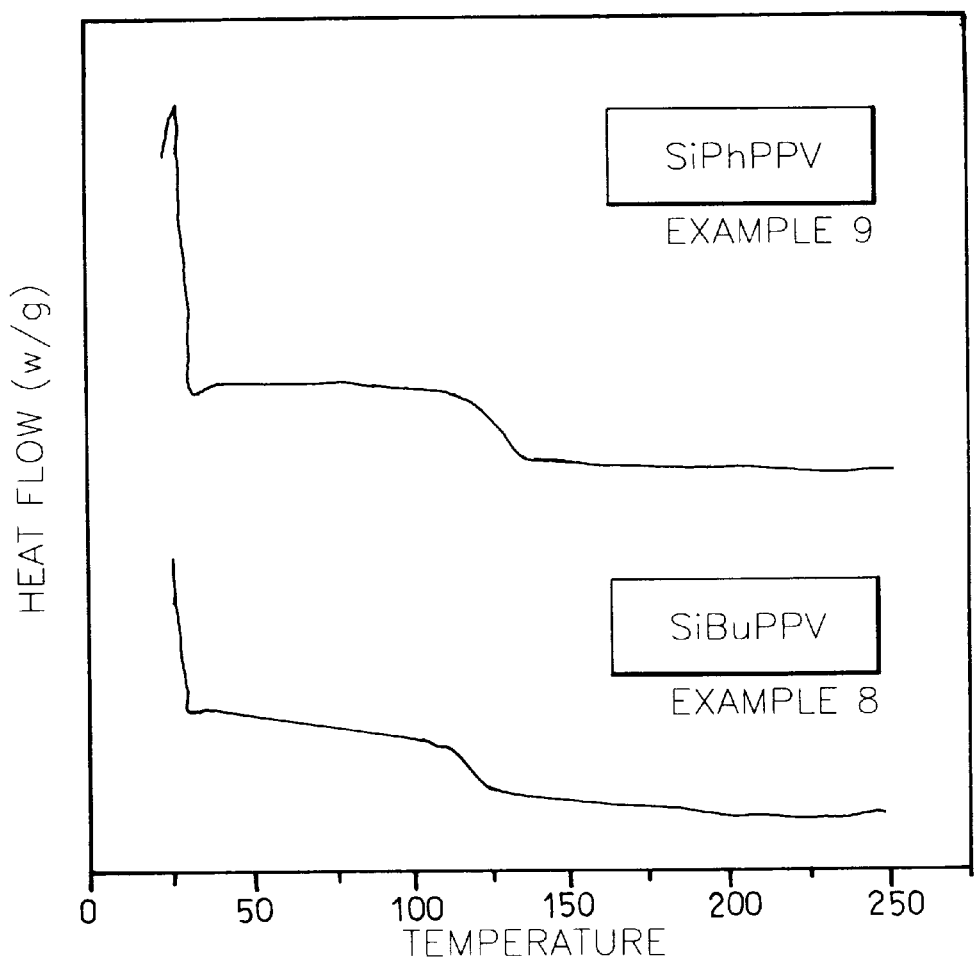
FIG. 1 is DSC spectra of the photoluminescence polymers which are prepared according to Examples 8 and 9.

The di-p-tolyldialkylsilane derivative of the chemical formula (1) is an organic silicon compound which is very useful as a monomer of a functional polymer.

Methods for preparing the di-p-tolyldialkylsilane derivative of the formula (1) and the photoluminescence polymer of the formula (2) formed from the derivative will be described.

First, dialkyldichlorosilane (A) and an organometallic compound (B) are reacted to obtain di-p-tolyldialkylsilane (C). For this reaction, ethers such as diethylether are used as a solvent, and a Grignard reagent or an organolithium compound is used as the organometallic compound.

Then, the di-p-tolyldialkylsilane (C) and a halogenation agent or a cyanation agent are reacted to obtain a di-p-tolyldialkylsilane derivative of the formula (1). Here, N-halosuccinic acid is used as the halogenating agent, and sodium cyanide is used as the cyanation agent. Preferably, a peroxide catalyst such as benzoyl peroxide is used in the reaction between the di-p-tolyldialkylsilane derivative (C) and the halogenating agent. Also, as the solvent, an inert solvent such as carbon tetrachloride ($CCl_4$) is used.

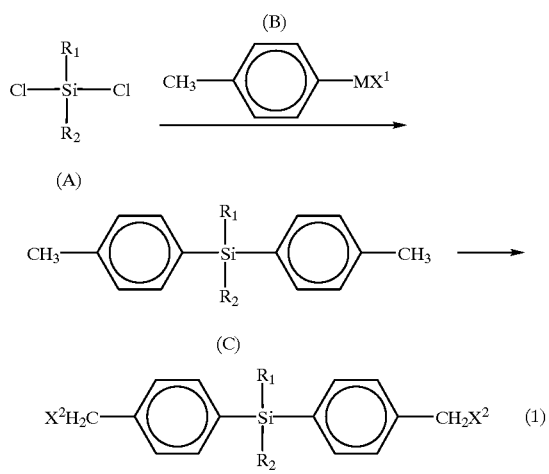

where $R_1$, $R_2$, M, $X^2$ and $X^2$ are the same as defined above.

The di-p-tolyldialkylsilane derivative of the chemical formula (1) is reacted with triphenylphosphine to form the corresponding phosphonium salt (D). Then, the obtained phosphonium salt (D) is reacted with dialdehyde compound (E) to obtain a photoluminescence polymer of the formula (2).

There is no limitation in selecting the dialdehyde compound (E). However, terephthalaldehyde, carbazolealdehyde, thiophenealdehyde, among others are preferably used.

where

$R_1$, $R_2$, $X^2$, $R_4$ and n are the same as defined above.

Hereinafter, examples of the present invention will be described. However, the present invention is not limited to the following examples.

Characteristics of new compounds prepared in the following Examples are evaluated as follows.

Structures of the compounds were identified by an IR spectroscopy and a $^1$H-NMR spectroscopy. Here, the $^1$H-NMR spectrum was obtained using a Brucker AM-200 and Brucker AM-300, and tetramethylsilane was used as an internal standard material.

The IR spectrum was obtained using a spectrometer (Perkin-Elmer), and the molecular weight was measured by gel permeation chromatography using Waters 510 and polystyrene was used as a standard material.

The UV absorption spectrum was obtained by using chloroform as a solvent and Shimadzu 3101PC spectrometer.

A fluorescence spectrum was obtained by Perkin-Elmer LS-spectrophotofluouometer. Here, a lokein amplifier having a pulse frequency of 150 Hz at room temperature was used as an amplifier, and a Xenon (X=351 nm) lamp was used as a light source.

Thermogravity analysis and differential scanning calorie analysis were performed using a Dupont 990 thermoanalyzer to which 951 TGA and 910S DSC modules were attached.

The melting point was measured using a Fisher-Jones melting point measuring device.

EXAMPLE 1

Synthesis of d-p-tolyldibutylsilane (DTBS)

20 g of dichlorodibutylsilane, 5.0 g of magnesium (Mg) and 43.4 ml of anhydrous ether were put into a 500 ml

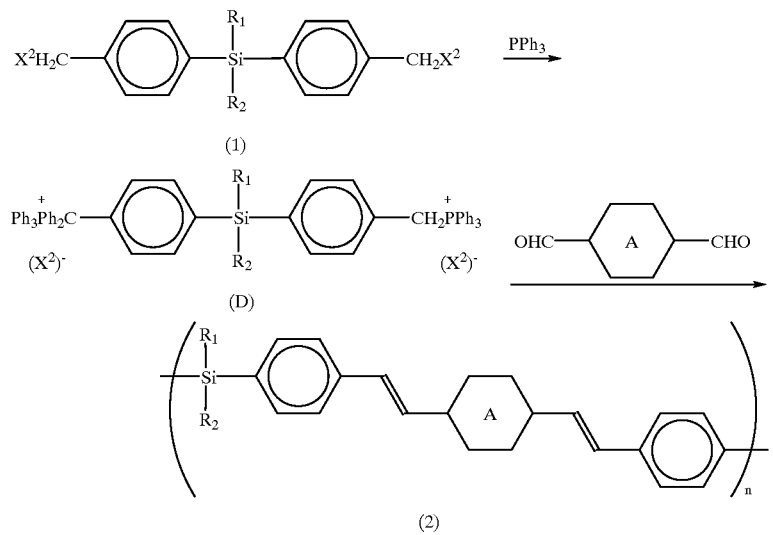

round-bottom flask, and then the resulting mixture was refluxed. A p-bromotoluene ether solution obtained by dissolving 35.5 g of p-bromotoluene in 18.5 ml of anhydrous ether was slowly dropped into the reaction mixture.

After refluxing the reaction mixture for 2 hours, ether was removed by vacuum distillation. Then, the reaction mixture was heated at 160° C. for 18 hours.

Then, cold water was added to the reaction mixture to form a precipitate, and the obtained precipitate was removed. Then, the reaction mixture was extracted with ether, and the obtained ether layer was washed with water, 5% HCl solution, 5% NaOH solution and water in sequence. After separating the water layer and the ether layer, the obtained ether layer was dried with anhydrous magnesium sulfate. Then, fractional distillation was performed to obtain fale yellow di-p-tolyldibutylsilane (Yield: 73%).

IR(neat, $cm^{-1}$): 1210, 964, 885 (Si-aliphatic); 1105, 750 (Si—Ph)
$^1$H-NMR (CDCl$_3$, ppm): 1.2~1.7 (m, 18H, Si-aliphatic); 2.7 (s, 6H, aryl CH); 7.5~7.8 (q, 8H, aryl CH)

EXAMPLE 2

Synthesis of di-p-tolyldiphenylsilane (DTPS)

38.1 g of dichlorodiphenylsilane and 4.2 g of lithium (Li) were placed into a 500 ml round bottom flask, and 60 ml of anhydrous ether was added to the mixture, and then refluxing was performed. Then, a p-bromotoluene ether solution obtained by dissolving 51.3 g of p-bromotoluene in 60 ml of anhydrous ether was slowly dropped into the reaction mixture.

After refluxing the reaction mixture for 3 hours, 9 ml of 10% HCl aqueous solution was added to remove excess Li.

After filtrating the reaction mixture, the solvent was removed through vacuum distillation to obtain a crude product. Then, the obtained crude product was recrystallized, resulting in 48 g of di-p-tolyldiphenylsilane in white powder form (Yield: 90%).

IR(KBr, $cm^{-1}$): 1425, 1105, 700 (Si—Ph)
$^1$H-NMR(DMSO-d$_6$, ppm): 2.25 (s, 6H, aryl CH); 7.2~7.6 (m, 18H, aryl CH)

EXAMPLE 3

Synthesis of di-(p-bromoethylphenyl)dibutylsilane 10 g of di-p-tolyldibutylsilane, 12.06 g of N-bromosuccinimide, 0.056 g of benzoyl peroxide were placed into 1000 ml round-bottom flask, and then the mixture was dissolved with 500 ml of carbon tetrachloride (CCl$_4$).

After refluxing the reaction mixture for 48 hours, the temperature was lowered to 50° C. to obtain a precipitate. The obtained precipitate, that is, succinimide, was removed. Then, the reaction mixture was distilled to remove the solvent, and then silicagel chromatography was performed with hexane/ethyl acetate (5:1 based on volume), resulting in 12 g of yellow di-(p-bromoethylphenyl)dibutylsilane (Yield: 74%).

IR(neat, $cm^{-1}$): 1210, 964, 885 (Si-aliphatic); 1105, 750 (Si—Ph); 1410, 1296, 798 (Ph—CH$_2$Br)
$^1$H-NMR (CDCl$_3$, ppm):0.8~1.4 (m, 18H, Si-aliphatic); 4.5 (s, 6H, aryl CH); 7.4~7.5 (q, 8H, aryl CH)

EXAMPLE 4

Synthesis of di-p-(bromomethylphenyl) diphenylsilane 3 g of di-p-tolyldibutylsilane, 2.9 g N-bromosuccinimide and 0.015 g of benzoylperoxide were placed into a 100 ml round bottom flask, and then the mixture was dissolved with 50 ml of carbon tetrachloride (CCl$_4$).

After refluxing the reaction mixture for 24 hours, the temperature was lowered to room temperature to obtain a precipitate. The obtained precipitate, that is, succinimide, was removed. Then, the reaction mixture was distilled to remove the solvent, and then washed with water.

The resultant was recrystallized with tetrachloride, resulting in 1.0 g of di-(p-bromoethylphenyl)diphenylsilane (Yield: 30%).

Melting point: 220° C.
IR(KBr, $cm^{-1}$): 1425, 1105, 700 (Si—Ph); 1296, 798 (Ph—CH$_2$Br) $^1$H-NMR (CDCl$_3$, ppm): 4.5 (s, 4H, aryl CH); 7.2–7.5 (m, 18H, aryl CH)

EXAMPLE 5

Synthesis of di-p-(cyanomethylphenyl)dibutylsilane 2 g of di-p-(brmomethylphenyl)dibutylsilane and 0.44 g NaCN were placed into a 100 ml round bottom flask, and then the mixture was refluxed for 24 hours.

After adding water to the reaction mixture, extraction with methylenechloride was performed. The extracted methylenechloride layer was washed with water and a saturated NaCl aqueous solution in sequence. After separating the water layer and the methylenechloride layer, the obtained methylenechloride layer was dried by using anhydrous magnesium sulfate. Then, the obtained resultant was distilled to remove the solvent, resulting in di-p-(cyanomethylphenyl)dibutylsilane (Yield: 80%).

IR(neat, $cm^{-1}$): 1210, 964, 885 (Si-aliphatic); 1105, 750 (Si— Ph); 2250 (Ph—CH$_2$CN)
$^1$H-NMR (CDCl$_3$, ppm): 0.8~1.4 (m, 18H, Si-aliphatic); 3.7 (s, 4H, aryl CH$_2$); 7.4 7.5 (q, 8H, aryl CH)

EXAMPLE 6

Synthesis of bis(p-tolyltriphenyl-phosphoniumbromide)dibutylsilane 2.15 g of di-p-(bromomethylphenyl)dibutylsilane and 2.57 g of triphenylphosphine were placed into a 100 ml round bottom flask, and then 10 ml of dimethylformamide (DMF) was added. Then, the mixture was refluxed for 24 hours.

After cooling the reaction mixture to room temperature, 500 ml of anhydrous ethylacetate was added to obtain a precipitate. The obtained precipitate was filtrated and drying was then performed at 40° C. for 2 days under a vacuum, resulting in bis(p-tolyltriphenylphosphonium-bromide) dibutylsilane (Yield: 55%).

IR(KBr, $cm^{-1}$): 1210, 964, 885 (Si-aliphatic); 1105, 750 (Si—Ph); 1410, 1296, 798 (Ph—CH$_2$Br); 1435, 741, 698 (PPh$_3$)
$^1$H-NMR (CDCl$_3$, ppm): 0.7~1.2 (m, 18H, Si-aliphatic); 5.1 (d, 4H, aryl CH); 7.0~8.0 (m, 38H, aryl CH)

EXAMPLE 7

Synthesis of bis(p-tolyltriphenylphosphonium-bromide)diphenylsilane 1.0 g of di-p-(bromomethylphenyl)diphenylsilane and 1.59 of triphenylphosphine were placed into a 100 ml round bottom flask, and 10 ml of DMF was added, and then the reaction mixture was refluxed for 24 hours.

After cooling the reaction mixture to room temperature, 300 ml of anhydrous ethylacetate was added to obtain a precipitate. The obtained precipitate was filtrated and then dried at 40° C. for 2 days under a vacuum, resulting in bis(p-tolyltriphenylphosphonium-bromide)diphenylsilane (Yield: 66%).

IR(KBr, cm$^{-1}$): 1425, 1105, 700 (Si—Ph); 1296, 798 (Ph—CH$_2$Br) 1435, 750, 685 (PPh$_3$)

$^1$H-NMR(CDCl$_3$, ppm): 5.4 (s, 4H, aryl CH); 7.1~7.8 (m, 40H, aryl CH)

EXAMPLE 8

Synthesis of the Polymer of the Formula (2) (;SiBuPPV when

is benzene and R$_1$ and R$_2$ are butyl group)

0.113 g of terephthalaldehyde (0.99 mmol) and 1.0 g of bis(4-triphenylphosphoniumtolylbromide)dibutylsilane (0.99 mmol) were placed into a 100 ml round bottom flask, and then dissolved with 30 ml of ethanol and 10 ml of chloroform. Then, sodium ethoxide solution obtained by dissolving 0.18 g of sodium (Na) in 10 ml of ethanol was dropwise added into the reaction mixture.

The reaction mixture was stirred for 12 hours, and then a pasty product formed on the wall of the flask was collected.

The product was dried in a vacuum oven to obtain a crude product. The crude product was dissolved in methylenchloride and then washed with water. Then, water and the methylenechloride layer were separated, and the obtained methylenechloride layer was dried with anhydrous magnesium sulfate.

After evaporating the solvent, the resultant was dried at 40° C. for 2 days in a vacuum oven, resulting in a yellow product (SiBuPPV) (Yield: 21%).

EXAMPLE 9

Synthesis of the Polymer of the Formula (2) (;SiPhPPV when

is benzene and R$_1$ and R$_2$ are phenyl group)

The product (SiPhPPV) was obtained by the same method as that of Example 8, except bis(4-triphenylphosphoniumtolylbromide)diphenylsilane, instead of bis(4-triphenylphosphoniumtolyl-bromide)dibutylsilane, was used (Yield: 26%).

EXAMPLE 10

The product was obtained by the same method as that of Example 9, except N-ethylhexyl 3,6-formylcarbazole, instead of terephthalaldehyde, was used (Yield: 27%).

EXAMPLE 11

The product was obtained by the same method as that of Example 9, except N-hexyl 3,6-formylcarbazole, instead of terephthalaldehyde, was used (Yield: 32%).

EXAMPLE 12

The polymer of the formula (5) was obtained by the same method as that of Example 9, except 2,5-thiophene carboxadialdehyde, instead of terephthalaldehyde, was used (Yield: 32%).

Figure 2:
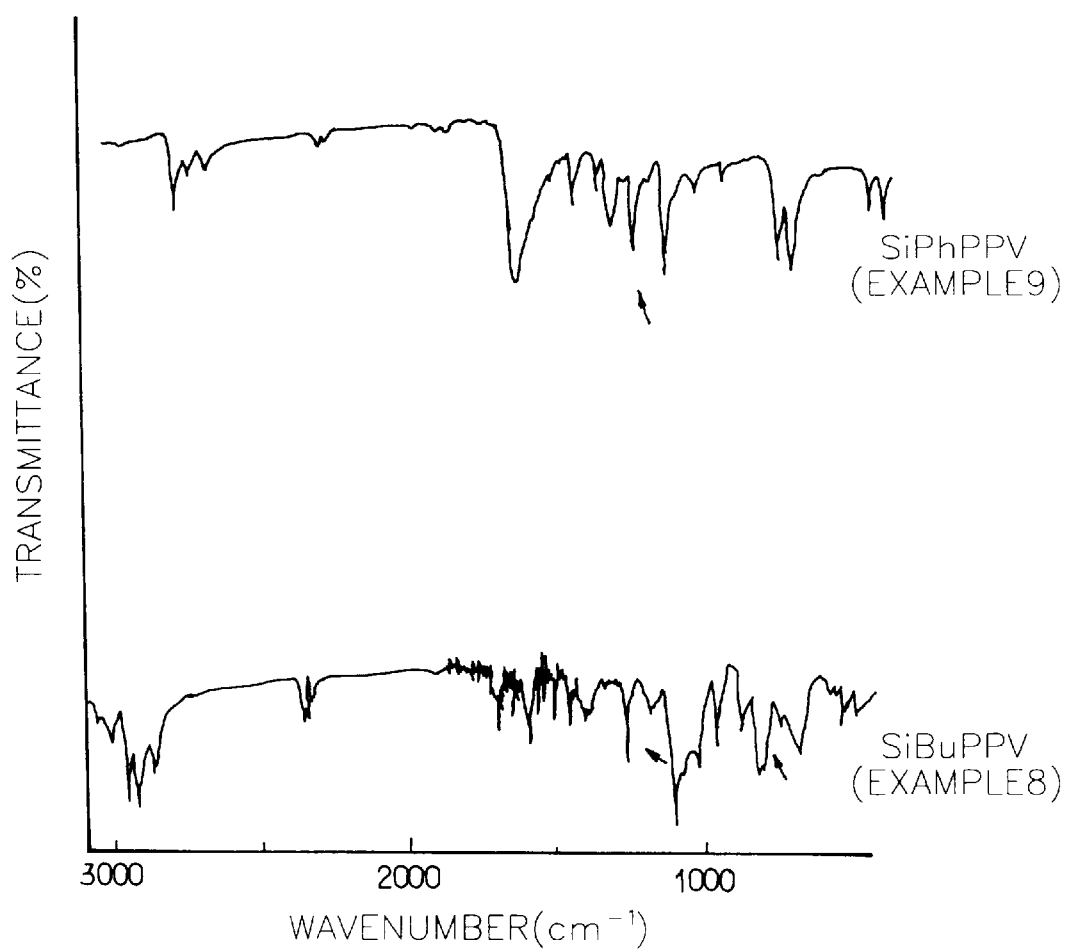
FIG. 2 is IR spectra of the photoluminescence polymers which are prepared according to Examples 8 and 9.
Figure 3A:
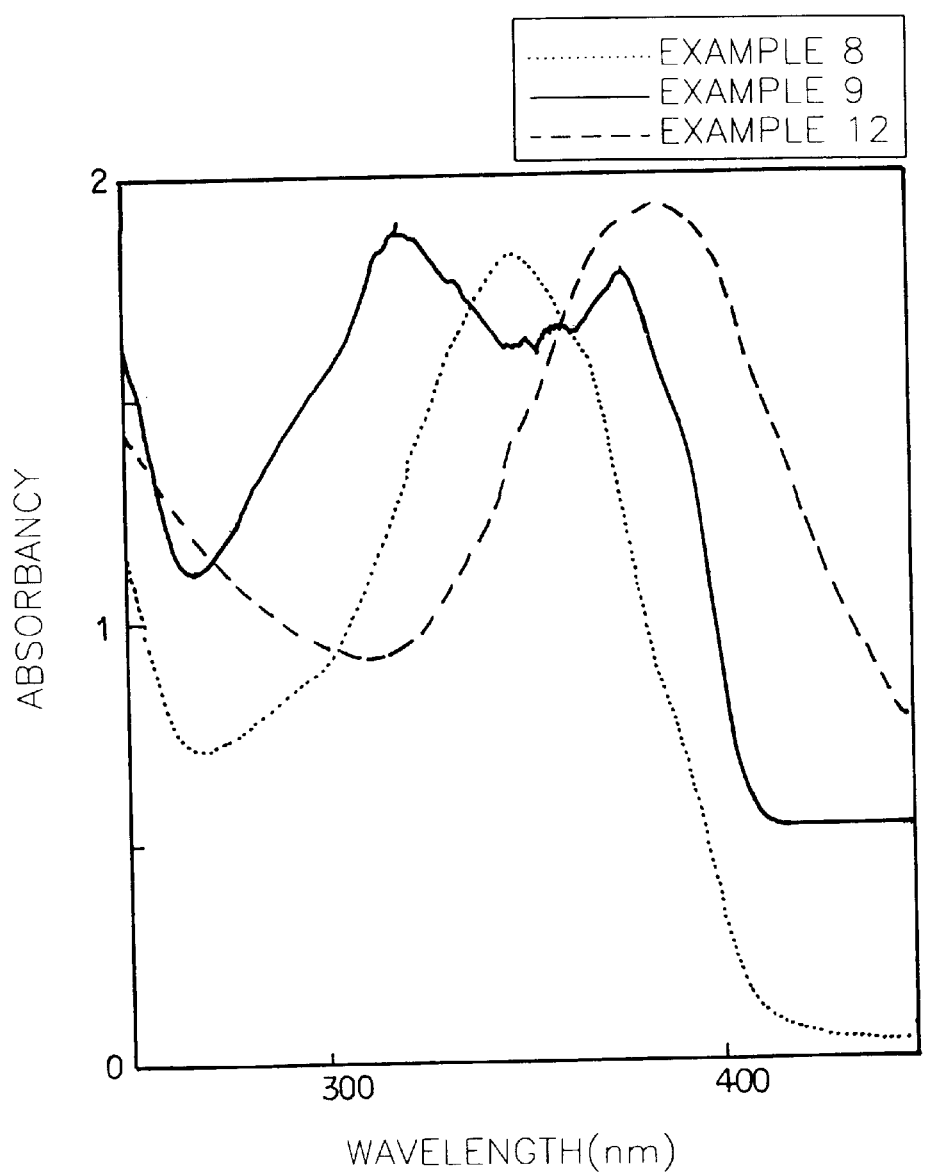
FIG. 3A is UV absorption spectra of the photoluminescence polymers prepared according to Examples 8, 9 and 12.
Figure 3B:
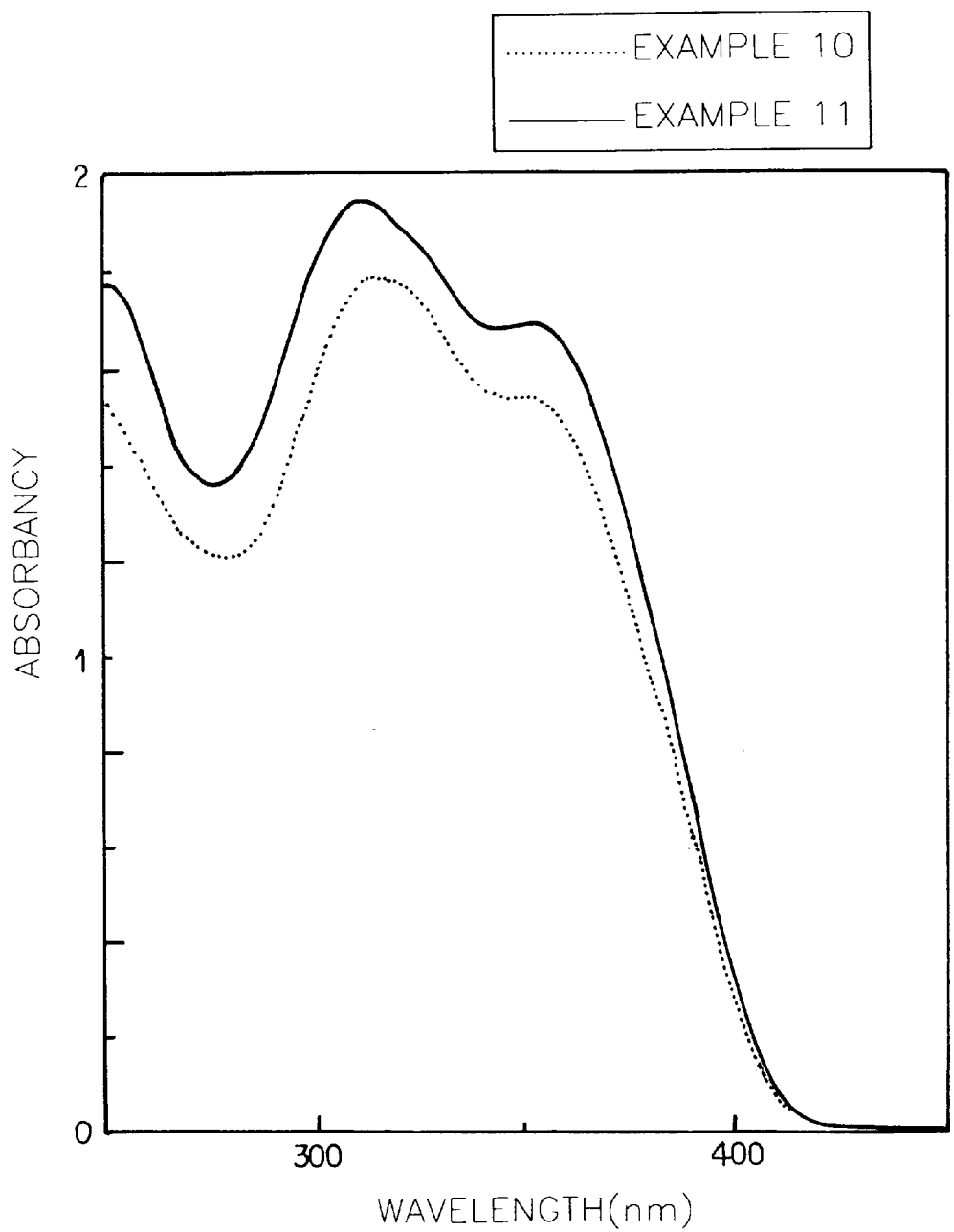
FIG. 3B is UV absorption spectra of the photoluminescence polymers prepared according to Examples 10 and 11.
Figure 4A:
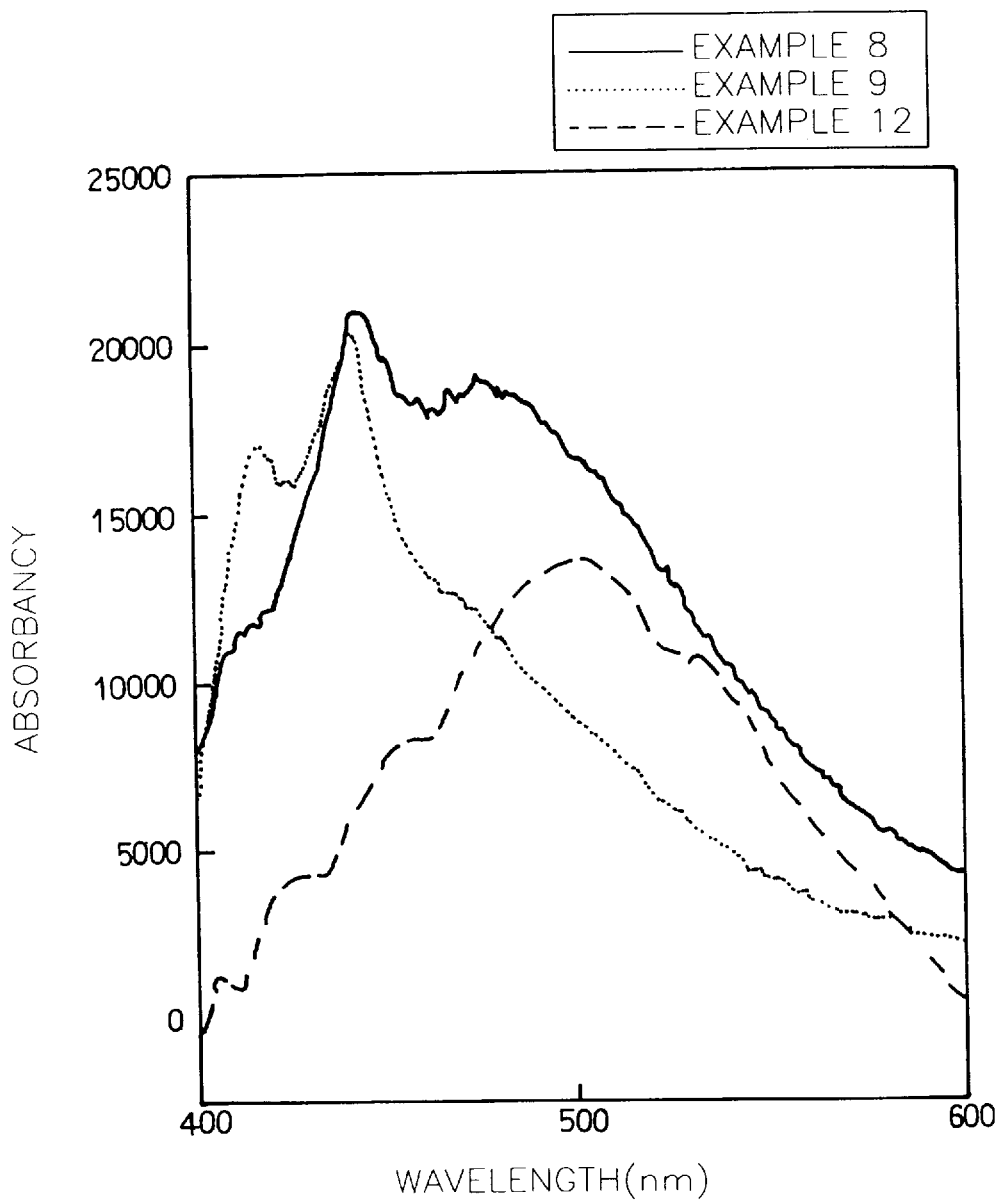
FIG. 4A is photoluminescence (PL) spectra of the photoluminescence polymers prepared according to Examples 8, 9 and 12.
Figure 4B:
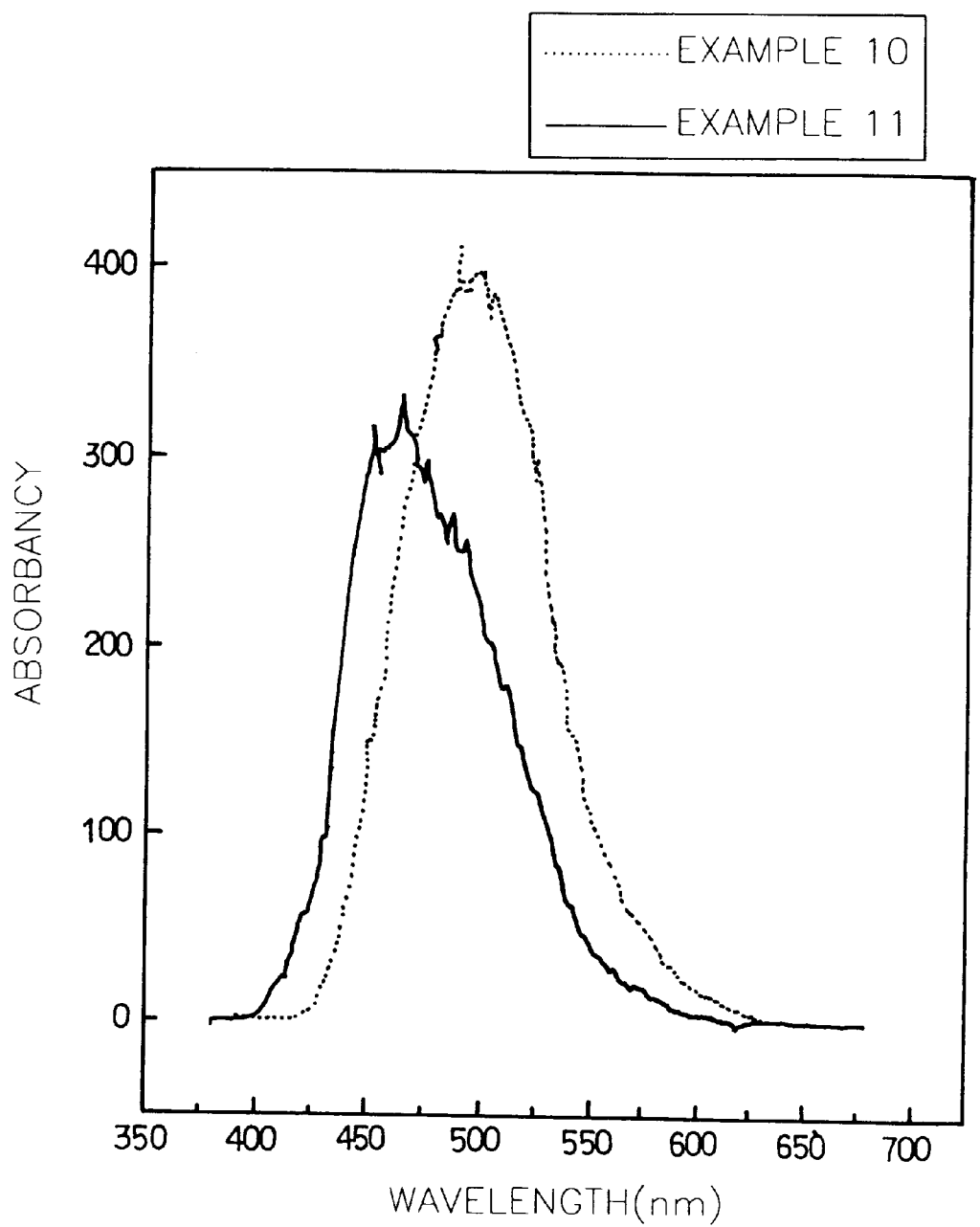
FIG. 4B is PL spectra of the photoluminescence polymers prepared according to Examples 10 and 11.

Spectrophotometric data of the polymers prepared by Examples 8~12, that is, the DSC, IR, NMR, UV absorption spectrum and photoluminescence (PL) spectrum, are shown in FIGS. 1 through 4.

Number average molecular weight (M$_n$), weight average molecular weight (M$_w$) and molecular weight distribution (M$_w$/M$_n$) of the polymers formed by Examples 8~12 are shown in Table 1.

TABLE 1

| class | M$_n$ | M$_w$ | M$_w$/M$_n$ |
| --- | --- | --- | --- |
| Example 8 | 2500 | 3700 | 1.48 |
| Example 9 | 2800 | 4100 | 1.50 |
| Example 10 | 2100 | 8300 | 3.8 |
| Example 11 | 1500 | 4500 | 3.0 |
| Example 12 | 1200 | 3700 | 3.0 |

As shown in Table 1, the number average molecular weight is of the polymers formed by Examples 8~12 was in the range of 1200~2800, the weight average molecular weight thereof was in the range of 3700~8300, and the molecular weight distribution thereof was in the range of 1.48~3.0.

On the other hand, T$_{de}$, char yield, glass transition temperature (T$_g$), and UV absorption spectrum and PL spectrum were measured and the results thereof are shown in Table 2. Here, T$_{de}$. represents the temperature at which loss in mass of the polymer begins, and the char yield is represented the following equation.

*char yield(%)=(the mass of residue after sample is heated to 600° C.) (g)/(the mass of starting sample ) (g)×100

TABLE 2

| Class | T$_{de}$(° C.) | char yield (%) | T$_g$(° C.) | UV λ$_{max}$ (nm) | PL λ$_{max}$ (nm) |
| --- | --- | --- | --- | --- | --- |
| Example 8 | 175 | 48 | 105 | 347 | 440 |
| Example 9 | 250 | 62 | 109 | 375 | 450, 480 |
| Example 10 | 178 | 44 | 108 | 353, 314 | 480 |
| Example 11 | 220 | 60 | 119 | 351, 311 | 420 |
| Example 12 | 240 | 64 | 116 | 387 | 520 |

From Table 2, the UV absorption spectra of the polymers formed by Examples 8~12 show the maximum absorption peak at 347~387 nm, and the PL spectra thereof show the maximum absorption peak at 420~520 nm. The photoluminescence polymers (Examples 8~9) such as PPV containing only silicon at its main chain show the PL peak in a blue region. Also, the photoluminescence polymers (Examples 10~11) containing carbazole and silicon at its main chain show the PL peak at 420 nm, which is shifted toward a short wavelength region compared to the polymers prepared by Examples 8~9. Also, the photoluminescence polymer (Example 12) containing thiophene show the PL peak at 520 nm, which is shifted toward a long wavelength region compared to the polymers of Examples 8~9.

The di-p-tolyldialkylsilane derivative of the chemical formula (1) is very useful as a monomer of a functional polymer. The photoluminescence polymer of the formula (2) formed from the di-p-tolyldialkylsilane derivative of the chemical formula (1) contains a silicon between the conjugated double bonds, thereby suppressing electron movement of the conjugated double bond. As a result, a range of colors between blue and green, particularly, blue, can be obtained. Also, when the photoluminescence polymer is adopted as a color developing substance, the threshold voltage characteristics are improved compared to a general photoluminescence polymer.

What is claimed is:

1. A di-p-tolyldialkylsilane derivative represented by the following formula (1):

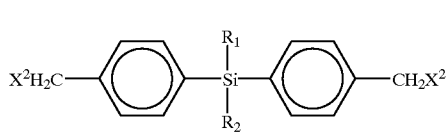

wherein $R_1$ and $R_2$ are independently selected from the group consisting of methyl, butyl, and phenyl and groups, and $X^2$ is selected from the group consisting of hydrogen, a halogen atom, and a cyano group.

2. A photoluminescence polymer comprising a repeating unit having silicon between conjugated double bonds, represented by the following formula (2):

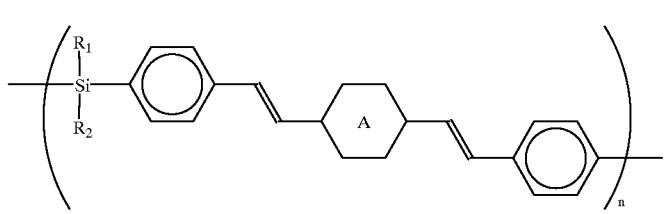

where

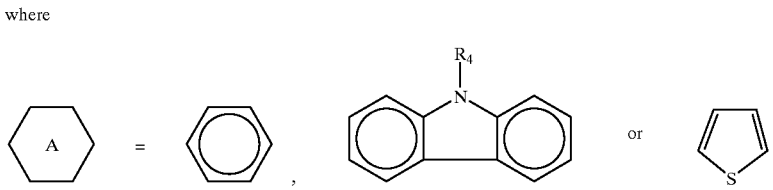

$R_1$ and $R_2$ are independently selected from the group consisting of phenyl and —(CH=CH)$_k$R$_3$ (k is an integer from 0 to 2, and $R_3$ is hydrogen or alkyl), $R_4$ is selected from the group consisting of hydrogen, an unsubstituted or substituted aliphatic hydrocarbon group, and an unsubstituted or substituted aromatic hydrocarbon group, and n is an integer from 1 to 100.

3. The photoluminescence polymer of claim 2, wherein the weight average molecular weight is between 1000 and 20000.

4. The photoluminescence polymer of claim 2, wherein

is benzene, and $R_1$ and $R_2$ are phenyl group.

5. The photoluminescence polymer of claim 2, wherein

is N-alkylcarbazole, and $R_1$ and $R_2$ are phenyl group.

6. The photoluminescence polymer of claim 2, wherein

is thiophene, and $R_1$ and $R_2$ are phenyl group.

7. A method for preparing a di-p-tolyldialkylsilane derivative of the formula (1), the method comprising:

(a) reacting a dialkyldichlorosilane (A) with an organometallic compound (B) to obtain a di-p-tolyldialkylsilane (C); and (b) reacting the di-p-tolyldialkylsilane (C) with a halogenating agent or a cyanation agent,

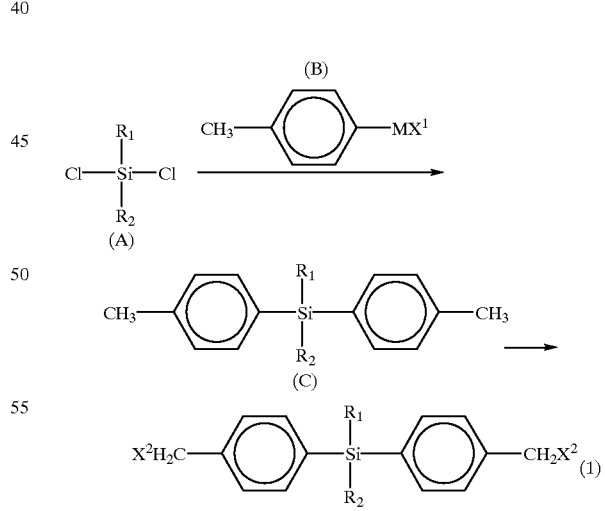

where $R_1$ and $R_2$ are independently selected from the group consisting of phenyl and —(CH=CH)R$_3$ (k is an integer from 0 to 2, and $R_3$ is hydrogen or alkyl group), M is magnesium (Mg) or lithium (Li), $X^1$ is chloride (Cl), bromide (Br) or iodide (I), and $X^2$ is hydrogen, Cl, Br, I or cyanide (CN).

8. The method of claim 7, wherein $R_1$ and $R_2$ are independently selected from the group consisting of methyl, butyl and phenyl groups.

9. A method for preparing a photoluminescence polymer of the formula (2), the method comprising:
(a) reacting a di-p-tolyldialkylsilane derivative of the formula (1) with triphenylphosphine to form the corresponding phosphonium salt (D); and
(b) reacting the obtained phosphonium salt (D) with a dialdehyde compound (E),

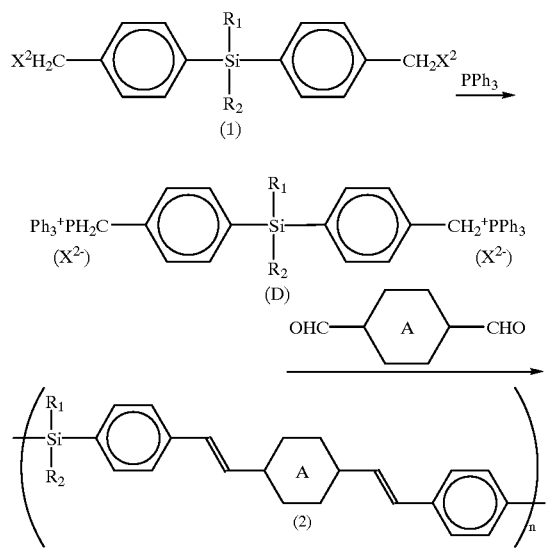

where

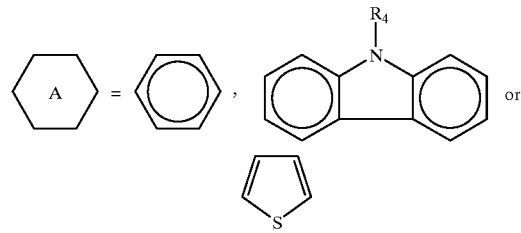

$R_1$ and $R_2$ are independently selected from the group consisting of phenyl and —(CH=CH)$_k$R$_3$ (k is an integer from 0 to 2, and $R_3$ is hydrogen or alkyl), $X^2$ is selected from the group consisting of hydrogen, a halogen atom and a cyano group, and $R_4$ is selected from the group consising of hydrogen, an unsubstituted or substituted aliphatic hydrocarbon group, and an unsubstituted or substituted aromatic hydrocarbon group, and n is an integer from 1 to 100.

10. The method of claim 9, wherein the weight average molecular weight is between 1000 and 20000.

11. The method of claim 9, wherein

is benzene, $R_1$ and $R_2$ are each independently a phenyl group.

12. The method of claim 9, wherein

is N-alkylcarbazole, $R_1$ and $R_2$ are each independently a phenyl group.

13. The method of claim 9, wherein

is thiophene, $R_1$ and $R_2$ are each independently a phenyl group.

* * * * *